United States Patent
Yamada et al.

(10) Patent No.: US 11,083,757 B2
(45) Date of Patent: Aug. 10, 2021

(54) INHIBITOR FOR COGNITIVE FUNCTION DECLINE

(71) Applicant: ZERIA PHARMACEUTICAL CO., LTD., Chuo-ku (JP)

(72) Inventors: Kotaro Yamada, Chuo-ku (JP); Hidetomo Sakurai, Chuo-ku (JP); Osamu Nakagawasai, Sendai (JP); Koichi Tanno, Sendai (JP)

(73) Assignee: ZERIA PHARMACEUTICAL CO., LTD., Chuo-ku (JP)

( * ) Notice: Subject to any disclaimer, the term of this patent is extended or adjusted under 35 U.S.C. 154(b) by 109 days.

(21) Appl. No.: 16/345,401

(22) PCT Filed: Oct. 27, 2017

(86) PCT No.: PCT/JP2017/038831
§ 371 (c)(1),
(2) Date: Apr. 26, 2019

(87) PCT Pub. No.: WO2018/079695
PCT Pub. Date: May 3, 2018

(65) Prior Publication Data
US 2019/0247442 A1    Aug. 15, 2019

(30) Foreign Application Priority Data

Oct. 28, 2016 (JP) .............................. JP2016-211301

(51) Int. Cl.
| | | |
|---|---|---|
| *A61K 35/18* | (2015.01) | |
| *A61K 35/12* | (2015.01) | |
| *A61K 35/00* | (2006.01) | |
| *A61K 35/407* | (2015.01) | |
| *A61P 25/00* | (2006.01) | |
| *A23L 33/115* | (2016.01) | |
| *A61K 9/00* | (2006.01) | |
| *A23L 5/00* | (2016.01) | |
| *A61P 25/28* | (2006.01) | |

(52) U.S. Cl.
CPC .............. *A61K 35/407* (2013.01); *A23L 5/00* (2016.08); *A23L 33/115* (2016.08); *A61K 9/0056* (2013.01); *A61P 25/00* (2018.01); *A61P 25/28* (2018.01); *A23V 2002/00* (2013.01)

(58) Field of Classification Search
None
See application file for complete search history.

(56) References Cited

U.S. PATENT DOCUMENTS

2010/0087383 A1    4/2010    Nitta et al.

FOREIGN PATENT DOCUMENTS

| JP | 2006-096747 A | 4/2006 |
|---|---|---|
| JP | 2016-135757 A | 7/2016 |
| JP | 2017/038831 | 10/2017 |
| WO | WO 2008/050754 A1 | 5/2008 |
| WO | WO 2015/022927 A1 | 2/2015 |
| WO | WO 2015/046184 A1 | 4/2015 |
| WO | WO 2016/068267 A1 | 5/2016 |

OTHER PUBLICATIONS

Wasaburo et al. (JP 2016-135757, p. 1, English abstract and claims Jul. 28, 2016, within the IDS) (Year: 2016).*
Abstracts of The 136th Annual Meeting of The Pharmaceutical Society of Japan (Yokohama) 38R-pm 19 and LS24 with English translation 2 pages (Year: 2021).*
International Search Report dated Jan. 16, 2018 in PCT/JP2017/038831 filed on Oct. 27, 2017.
Pharmaceutical Product Interview Form (Aricept) with partial English translation (Total 8 pages).
Abstracts of the 136th Annual Meeting of the Pharmaceutical Society of Japan (Yokohama) 28R-pm19 and LS24 with partial English translation (Total 5 pages).
Ahn, C.-B. et al., "Enzymatic production of bioactive protein hydrolysates from tuna liver: effects of enzymes and molecular weight on bioactivity," International Journal of Food Science and Technology, vol. 45, 2010, pp. 562-568.
Inoue, N. et al., "Analysis of the Components of Porcine Liver Hydrolysate and Examination of the Antioxidant Activity and Angiotensin Converting Enzyme (ACE)-inhibiting Activity," The Pharmaceutical Society of Japan, Yakugaku Zasshi, vol. 133, No. 1, 2013, pp. 107-115.
Du, L.-L. et al., "AMPK Activation Ameliorates Alzheimer's Disease-Like Pathology and Spatial Memory Impairment in a Streptozotocin-Induced Alzheimer's Disease Model in Rats," Journal of Alzheimer's Disease, vol. 43, 2015, pp. 775-784.
Vingtdeux, V. et al., "AMP-activated Protein Kinase Signaling Activation by Resveratrol Modulates Amyloid-β Peptide Metabolism," Journal of Biological Chemistry, vol. 285, No. 12, 2010, pp. 9100-9113. (Total 15 pages).

* cited by examiner

*Primary Examiner* — Michael Barker
*Assistant Examiner* — Randall O Winston
(74) *Attorney, Agent, or Firm* — Oblon, McClelland, Maier & Neustadt, L.L.P.

(57) ABSTRACT

A cognitive decline inhibitor or a learning ability improver is provided, which comprises, as an active ingredient, a liver hydrolysate having a lipid content of less than 2 mass % or a phosphatidylcholine content of less than 1 mass %.

14 Claims, 1 Drawing Sheet

INHIBITOR FOR COGNITIVE FUNCTION DECLINE

TECHNICAL FIELD

The present invention relates to a cognitive decline inhibitor and a learning ability improver.

BACKGROUND ART

Examples of dementia include vascular dementia, Alzheimer-type dementia, dementia with Lewy bodies, Parkinson's disease involving dementia, and frontotemporal dementia. Core symptoms of dementia include memory impairment, disorientation, and cognitive impairment, and peripheral symptoms include hallucination, delusion, wandering, abnormal eating behavior, sleep disorder, depression, anxiety, irritation, rantings, violence, and a decreased sense of sexual shame, for example.

As therapeutic agents for dementia, acetylcholinesterase inhibitors (donepezil, galantamine, and rivastigmine) and an NMDA receptor antagonist (memantine) are employed as drugs for improvement of cognitive functions. However, these medicines have adverse effects such as adverse effects of gastrointestinal symptoms including nausea or vomiting, anorexia, diarrhea, abdominal pain and the like at high incidences (Non Patent Literature 1).

CITATION LIST

Non Patent Literature

Non Patent Literature 1: Pharmaceutical Product Interview Form (Aricept)
Non Patent Literature 2: Abstracts of The 136$^{th}$ Annual Meeting of The Pharmaceutical Society of Japan (Yokohama) 28R-pm19 and LS24

SUMMARY OF THE INVENTION

Technical Problem

An object of the present invention is to provide a cognitive function improver with reduced adverse effects.

Solution to Problem

Accordingly, the present inventors have examined ingredients with a high safety profile for the presence or absence of the effect concerning cognitive functions. It has been reported that administration of a phosphatidylcholine-rich swine hepatic degradation product to patients may improve cognitive functions (Non Patent Literature 2). This does not confirm the hepatic degradation product's own effect, but is the result of examining the effect of phosphatidylcholine contained rich in this special hepatic degradation product. On the other hand, the present inventors have examined the effects of various natural ingredients using cognitive decline model mice, bulbectomized mice. As a result, the present inventors have completely surprisingly found that a liver hydrolysate with a low content of a lipid such as phosphatidylcholine has excellent effect of inhibiting cognitive decline and improving learning ability, and thus have completed the present invention.

Specifically, the present invention provides the following [1] to [28].

[1] A cognitive decline inhibitor, comprising, as an active ingredient, a liver hydrolysate having a phosphatidylcholine content of less than 1 mass %.
[2] A learning ability improver, comprising, as an active ingredient, a liver hydrolysate having a phosphatidylcholine content of less than 1 mass %.
[3] A food composition for inhibiting cognitive decline, comprising, as an active ingredient, a liver hydrolysate having a phosphatidylcholine content of less than 1 mass %.
[4] A food composition for improving learning ability, comprising, as an active ingredient, a liver hydrolysate having a phosphatidylcholine content of less than 1 mass %.
[5] A cognitive decline inhibitor, comprising, as an active ingredient, a liver hydrolysate having a lipid content of less than 2 mass %.
[6] A learning ability improver, comprising, as an active ingredient, a liver hydrolysate having a lipid content of less than 2 mass %.
[7] A food composition for inhibiting cognitive decline, comprising, as an active ingredient, a liver hydrolysate having a lipid content of less than 2 mass %.
[8] A food composition for improving learning ability, comprising, as an active ingredient, a liver hydrolysate having a lipid content of less than 2 mass %.
[9] Use of a liver hydrolysate having a phosphatidylcholine content of less than 1 mass % for production of a cognitive decline inhibitor.
[10] Use of a liver hydrolysate having a phosphatidylcholine content of less than 1 mass % for production of a learning ability improver.
[11] Use of a liver hydrolysate having a phosphatidylcholine content of less than 1 mass % for production of a food composition for inhibiting cognitive decline.
[12] Use of a liver hydrolysate having a phosphatidylcholine content of less than 1 mass % for production of a food composition for improving learning ability.
[13] Use of a liver hydrolysate having a lipid content of less than 2 mass % for production of a cognitive decline inhibitor.
[14] Use of a liver hydrolysate having a lipid content of less than 2 mass % for production of a learning ability improver.
[15] Use of a liver hydrolysate having a lipid content of less than 2 mass % for production of a food composition for inhibiting cognitive decline.
[16] Use of a liver hydrolysate having a lipid content of less than 2 mass % for production of a food composition for improving learning ability.
[17] A liver hydrolysate having a phosphatidylcholine content of less than 1 mass %, for use in inhibiting cognitive decline.
[18] A liver hydrolysate having a phosphatidylcholine content of less than 1 mass %, for use in improving learning ability.
[19] A method for using a liver hydrolysate having a phosphatidylcholine content of less than 1 mass % for non-therapeutic inhibition of cognitive decline.
[20] A method for using a liver hydrolysate having a phosphatidylcholine content of less than 1 mass % for non-therapeutic improvement of learning ability.
[21] A liver hydrolysate having a lipid content of less than 2 mass %, for use in inhibiting cognitive decline.
[22] A liver hydrolysate having a lipid content of less than 2 mass %, for use in improving learning ability.
[23] A method for using a liver hydrolysate having a lipid content of less than 2 mass % for non-therapeutic inhibition of cognitive decline.

[24] A method for using a liver hydrolysate having a lipid content of less than 2 mass % for non-therapeutic improvement of learning ability.

[25] A method for inhibiting cognitive decline, comprising ingesting an effective amount of a liver hydrolysate having a phosphatidylcholine content of less than 1 mass %.

[26] A method for improving learning ability, comprising ingesting an effective amount of a liver hydrolysate having a phosphatidylcholine content of less than 1 mass %.

[27] A method for inhibiting cognitive decline, comprising ingesting an effective amount of a liver hydrolysate having a lipid content of less than 2 masse.

[28] A method for improving learning ability, comprising ingesting an effective amount of a liver hydrolysate having a lipid content of less than 2 mass %.

Effects of the Invention

According to the present invention, ingestion of a liver hydrolysate which has no adverse effect even when a large amount thereof is ingested can inhibit a symptom of dementia, cognitive decline, and can improve learning ability.

DESCRIPTION OF EMBODIMENTS

Figure 1:
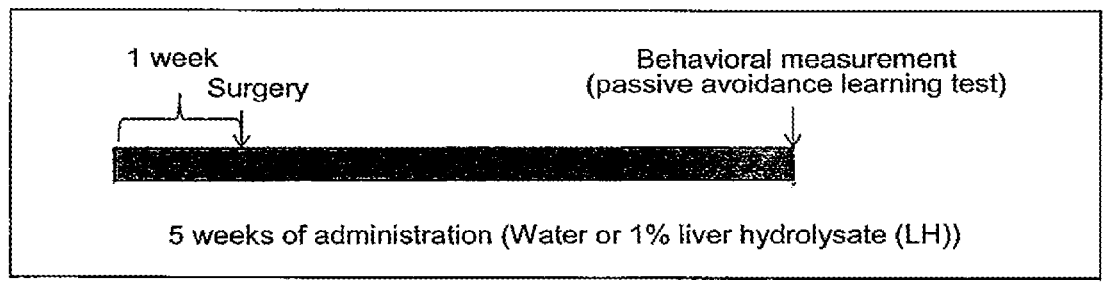
FIG. 1 shows the test protocol of Example 1.

The active ingredient of the cognitive decline inhibitor and the learning ability improver of the present invention is a liver hydrolysate having a phosphatidylcholine content of less than 1 mass % or a lipid content of less than 2 mass %. The phosphatidylcholine content can be specified by measuring the amount of phospholipids including phosphatidylcholine. The phosphatidylcholine content is less than 1 mass %, more preferably 0.5 mass % or less, and even more preferably 0.25 mass % or less. Moreover, the lipid content is less than 2 mass %, more preferably 1 mass % or less, and even more preferably 0.5 mass % or less.

The liver hydrolysate is also referred to as a hydrolyzed liver, a liver extract, a hydrolyzed liver extract, or a hepatic hydrolysate, obtained by hydrolysis of the liver with a digestive enzyme etc., and used as a drug for improving liver functions. Fresh bovine, swine, bonito, or whale liver, etc., is used as a raw material liver. The thus obtained hydrolysate is preferably concentrated and then used. Preferable examples of the liver hydrolysate include liver hydrolysates that have been defined as the above pharmaceutical products.

The liver hydrolysate contains a low-molecular-weight peptide as the main ingredient, various amino acids, nucleotides, vitamins, minerals, and the like. More specifically, the liver hydrolysate preferably contains 19 to 78 mass % of amino acids, 17 to 73 mass % of peptides and proteins, 1.8 to 11 mass % of saccharides, 0.005 to 0.04 mass % of lipids, 0.7 to 2.5 masse % of nucleic acids, 1.6 to 5.4 mass % of inorganic matter, 0.03 to 0.2 mass % of vitamins, and 0.8 mass % or less of glutathione. The liver hydrolysate more preferably contains 23 to 65 mass % of amino acids, 20 to 61 mass % of peptides and proteins, 2.2 to 8.6 mass % of saccharides, 0.006 to 0.035 mass % of lipids, 0.9 to 2.1 masse of nucleic acids, 1.9 to 4.5 mass % of inorganic matter, 0.04 to 0.15 masse of vitamins, and 0.7 mass % or less of glutathione, and even more preferably contains 29 to 52 mass % of amino acids, 25 to 49 mass % of peptides and proteins, 2.8 to 6.9 mass % of saccharides, 0.008 to 0.03 mass % of lipids, 1.1 to 1.7 mass % of nucleic acids, 2.4 to 3.6 mass % of inorganic matter, 0.05 to 0.12 mass % of vitamins, and 0.6 mass % or less of glutathione.

Of these ingredients, the composition of amino acids is as follows: preferably, 17 to 68 mg/g of Ala, 0.6 to 4.4 mg/g of Arg, 9 to 48 mg/g of Asp, 5 mg/g or less of cystine, 18 to 63 mg/g of Glu, 10 to 39 mg/g of Gly, 3 to 17 mg/g of His, 14 to 56 mg/g of Ile, 26 to 98 mg/g of Leu, 15 to 65 mg/g of Lys, 0.3 to 20 mg/g of Met, 13 to 46 mg/g of Phe, 10 to 48 mg/g of Pro, 12 to 49 mg/g of Ser, 12 to 45 mg/g of Thr, 3 to 13 mg/g of Trp, 1.6 to 41 mg/g of Tyr, and 18 to 71 mg/g of Val; more preferably, 21 to 57 mg/g of Ala, 0.8 to 3.6 mg/g of Arg, 11 to 40 mg/g of Asp, 4 mg/g or less of cystine, 22 to 53 mg/g of Glu, 13 to 32 mg/g of Gly, 4 to 14 mg/g of His, 17 to 47 mg/g of Ile, 32 to 82 mg/g of Leu, 18 to 54 mg/g of Lys, 0.4 to 17 mg/g of Met, 15 to 38 mg/g of Phe, 12 to 40 mg/g of Pro, 15 to 41 mg/g of Ser, 14 to 38 mg/g of Thr, 3.8 to 11 mg/g of Trp, 1.9 to 34 mg/g of Tyr, and 21 to 59 mg/g of Val; and even more preferably, 26 to 45 mg/g of Ala, 1 to 2.9 mg/g of Arg, 14 to 32 mg/g of Asp, 3 mg/g or less of cystine, 27 to 42 mg/g of Glu, 16 to 26 mg/g of Gly, 5 to 11 mg/g of His, 21 to 40 mg/g of Ile, 40 to 66 mg/g of Leu, 22 to 43 mg/g of Lys, 0.5 to 14 mg/g of Met, 19 to 31 mg/g of Phe, 15 to 32 mg/g of Pro, 18 to 33 mg/g of Ser, 18 to 30 mg/g of Thr, 4.8 to 8.4 mg/g of Trp, 2.4 to 27 mg/g of Tyr, and 27 to 48 mg/g of Val.

The above liver hydrolysate exhibited an effect of inhibiting cognitive decline in the dementia model mice, bulbectomized mice, as described later in Examples. The liver hydrolysate also exhibited an effect of improving the learning ability of normal mice. Therefore, a liver hydrolysate having a phosphatidylcholine content of less than 1 mass % or a lipid content of less than 2 mass % is useful as a cognitive decline inhibitor or a learning ability improver.

Examples of cognitive impairment include memory impairment and disorientation (disorientation in time, location and person), decreased arithmetic skills, impaired judgment, aphasia, agnosia, apraxia, and executive function disorder. Examples of learning ability include memory, orientation, arithmetic skills, and judgment.

The cognitive decline inhibitor and/or the learning ability improver of the present invention can be administered by oral administration, percutaneous administration, enteral administration, intravenous administration, or the like, and is more preferably administered by oral administration. Examples of a preparation for oral administration include solutions, tablets, powders, fine granules, granules, and capsules. Solutions and tablets are preferable and solutions are more preferable.

For the formulation of these preparations for oral administration, an excipient such as lactose, mannitol, corn starch, and crystalline cellulose, a binder such as a cellulose derivative, gum Arabic, and gelatin, a disintegrator such as carboxymethylcellulose calcium, a lubricant such as talc and magnesium stearate, a solubilizing agent such as nonionic surfactant, a flavoring agent, a sweetening agent, a stabilizer, a pH adjusting agent, water, ethanol, propylene glycol, glycerin and the like can be used. Moreover, a coating such as hydroxymethyl cellulose phthalate, hydroxypropyl methylcellulose acetate succinate, cellulose acetate phthalate, and methacrylate copolymer can also be used.

Furthermore, the cognitive decline inhibitor and/or the learning ability improver of the present invention can also contain other active ingredients. Examples of the other active ingredients include: $B_1$ vitamins such as thiamine, thiamine nitrate, thiamine hydrochloride, fursultiamine, bisbentiamine, benfotiamine, thiamine disulfide, dicethiamine, thiamine propyl disulfide and derivatives thereof; vitamins $B_2$ such as riboflavin and its derivatives, and salts thereof; vitamins $B_3$ such as niacin, nicotinic acid, nicotinamide and its derivatives, and salts thereof; vitamins $B_5$ such as panthenol, pantothenic acid and its derivatives, and salts thereof; vitamins Be such as pyridoxine and its derivatives, and salts thereof; vitamins $B_{12}$ such as cyanocobalamin and its derivatives, and salts thereof; and other vitamins such as vitamin A, vitamin C, vitamin E, vitamin K, and vitamin P; and diisopropylamine dichloroacetate, taurine, chondroitin sulfate, royal jelly, caffeine, turmeric, milk thistle, dandelion, western dandelion, burdock, garlic, chrysanthemum, yarrow, gardenia, sesame, Tashichi ninjin (*Panax notoginseng* Berk), asparagus, onion, chicory, sage, artichoke, Chinese desert-thorn, plants of the family Fabaceae and plants of the family Iridaceae, miyamauzura (Goodyera schlechtendaliana), erva de passarinho, sete-sangria, Japanese Mallotus, black tea, resveratrol, catechins, berberine, rosemary, bean extract, metformin, yolk lecithin, DHA, EPA, ARA, vitamin D, ginkgo, ferulic acid, hydrogen, plasmalogen, garden angelica, and bacopa monniera.

Moreover, the cognitive decline inhibitor and/or the learning ability improver of the present invention can also be used as, in addition to pharmaceutical products, quasi drugs, and food compositions for functional foods, such as foods for specified health uses, foods for children, sports drinks, beverages for rehabilitation, and pet foods.

The content of the liver hydrolysate in the cognitive decline inhibitor and/or the learning ability improver of the present invention varies depending on dosage forms, and generally ranges from preferably 0.001 to 10 mass % in dry weight, and more preferably 0.001 to 5 mass % in dry weight. Furthermore, the daily dose for an adult of the liver hydrolysate in the cognitive decline inhibitor and/or the learning ability improver of the present invention ranges from preferably 3 g to 10 g in dry weight, more preferably 3.5 g to 8 g in dry weight, and even more preferably 4 g to 7.5 g in dry weight.

EXAMPLES

The present invention will be described more specifically by way of Examples as follows, but the present invention is not limited thereto.

Reference Example 1

The choline level of a liver hydrolysate was measured according to the following assay for phospholipid level.

Phospholipid was determined using Phospholipids C-Test Wako (Wako Pure Chemical Industries, Ltd., Pharmaceutical product for external diagnosis) (Takayama et al., 1977). Specifically, a reference solution of choline chloride (54 mg/100 mL) (corresponding to phospholipid 300 mg/100 mL) included in a measurement kit of Phospholipids C-Test Wako was diluted with water for adjustment, thereby preparing a standard solution. About 0.1 g of a sample was precisely weighed, water was added to the sample to dissolve in such a manner that the volume was precisely 10 mL, thereby preparing a sample solution. However, when a sample was not dissolved in water, 5 mL of water was added, ultrasonic wave was used for uniform dispersion, and then water was added in such a manner that the volume was precisely 10 mL. The solution was filtered using a membrane filter with a pore size of 0.45 μm or less. The initial filtrate (2 mL) was removed, and the next filtrate was used as a sample solution. Twenty L of the standard solution and 20 μL of the sample solution were weighed, and then 3 mL of a chromogenic test solution was precisely added to each of them. The solutions were shaken and mixed well and then heated at 37° C. for 5 minutes. Water (20 μL) was similarly treated to prepare a control solution with respect to these solutions, and then the solutions were tested by ultraviolet-visible spectrophotometry. Each of the solutions obtained from the standard solution and the sample solution was measured at a wavelength of 600 nm, thereby measuring absorbance $A_S$ and absorbance $A_T$. A calibration curve was prepared from the absorbances corresponding to each of the standard solutions, and then a choline chloride level corresponding to absorbance $A_T$ was found from the regression equation.

Example 1

(1) Experimental Animal

Male ddY mice (Japan SLC Inc.) each weighing 28 to 30 g were used for the experiment. The mice were kept under a constant environment: room temperature of 22±2° C., humidity of 55±5%, light and dark cycle of 12 hours (light period: 7:00 to 19:00, and dark period: 19:00 to 7:00) before experiment. The animals were kept in plastic cages (length of 30 cm×width of 20 cm×height of 15 cm) each containing 5 to 7 mice.

(2) Olfactory Bulbectomy

After administration of Somnopentyl (50 mg/kg, i.p.) for general anesthesia, each mouse was immobilized to a brain stereotaxic apparatus, 2 small holes were drilled using a dentistry drill on the cranial bone immediately above the olfactory bulb (OB), ⅔ or more of the olfactory bulb including the anterior olfactory nucleus was removed by suction (C-12 suction pump manufactured by SHINKU KIKO Inc.). Subsequently, spongel (Astellas Pharma Inc.) was embedded to fill the holes and to stop bleeding, and then the mice were used for the experiment. To examine the influence of OBX surgery, mice that had not been subjected to OBX involving suction, but had been subjected to drilling of holes on the cranial bone without damaging the brain, and filling the holes with spongel were used as mice of a Sham group in the experiment. Note that mice having undergone OBX surgery were subjected to craniotomy after completion of the experiment, the brain was removed to confirm surgical sites, and then mice having injuries at the frontal cortex or mice with remaining olfactory bulb were excluded from data.

(3) Drug Used and Adjustment Method

The drug used was a liver hydrolysate (Zeria Pharmaceutical Co., Ltd.: phosphatidylcholine at a detection limit or lower) and tap water was used as a solvent. The liver hydrolysate was dissolved in tap water in such a manner that the concentration was 1%. Drug administration was performed via free feeding with a feed water bottle from 1 week before OBX surgery for a total of 5 weeks.

(4) Evaluation Method

Each mouse was placed facing away from the guillotine door in a light room of a passive avoidance system, and then the mouse passed through the guillotine door and moved into a dark room. After confirming that the mouse had completely moved in the dark room with its extremities on the metal grid, electrical stimulation (1 mA, 500 sec) was applied. This was considered to be a learning trial. After the learning trial, mice were returned to the cages. The olfactory bulb was removed immediately after the learning trial. On day 28 after surgery, each OBX mouse was placed in a light room in a manner similar to that in the learning trial, and then the time required for the mouse to enter the dark room, that is, the latency time, was measured. This was considered to be a test trial. The cut-off time for both learning trial and test trial was set at 10 minutes (FIG. 1).

(5) Statistical Processing

Experimental results were depicted with averages and standard errors. A significance test was carried out using Fisher's PLSD post-hoc test after analysis of variance, and a significance level of 5% or less was determined to be the presence of a significant difference. In addition, Stat view-J 5.0 was used for these tests.

(6) Results

Figure 2:
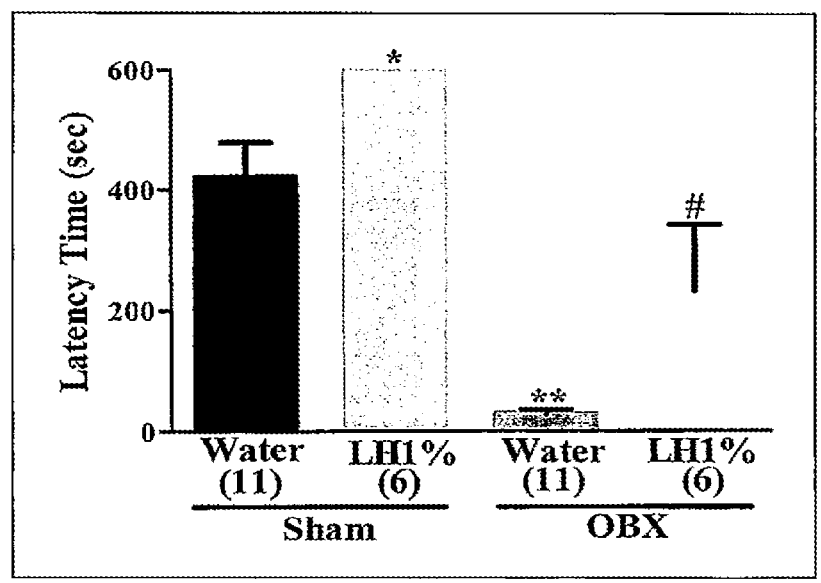
FIG. 2 shows the test results of Example 1.

FIG. 2 shows the results.

On day 28 after surgery (4 weeks), the latency time (response latency time) of the OBX group to which the solvent had been administered significantly decreased (**$p<0.01$) compared with the Sham group to which the solvent had been administered.

The OBX group to which 1% liver hydrolysate had been administered exhibited a significantly prolonged latency time (#$p<0.05$) compared with the OBX group to which the solvent had been administered.

The Sham group to which 1% liver hydrolysate had been administered also exhibited a significantly prolonged latency time compared with the Sham group to which the solvent had been administered (*$p<0.05$).

The invention claimed is:

1. A method for improving cognitive function of a subject having a need therefor, comprising ingesting an effective amount of a liver hydrolysate, wherein the liver hydrolysate has (i) a phosphatidylcholine content of less than 0.5 mass %, and (ii) a lipid content of less than 2 mass %.

2. A method for improving learning ability of a subject having a need therefor, comprising ingesting an effective amount of a liver hydrolysate, wherein the liver hydrolysate has (i) a phosphatidylcholine content of less than 4-0.5 mass %, and (ii) a lipid content of less than 2 mass %.

3. The method of claim 1, wherein the liver hydrolysate has a phosphatidylcholine content of 0.25 mass % or less.

4. The method of claim 2, wherein the liver hydrolysate has a phosphatidylcholine content of 0.25 mass % or less.

5. The method of claim 1, wherein the liver hydrolysate has a lipid content of 1 mass % or less.

6. The method of claim 2, wherein the liver hydrolysate has a lipid content of 1 mass % or less.

7. The method of claim 1, wherein the effective amount of the liver hydrolysate is a daily dose of 3 g to 10 g in dry weight.

8. The method of claim 2, wherein the effective amount of the liver hydrolysate is a daily dose of 3 g to 10 g in dry weight.

9. A method for improving a subject's cognitive function, comprising administering an effective amount of a liver hydrolysate, wherein the liver hydrolysate has (i) a phosphatidylcholine content of less than 0.5 mass %, and (ii) a lipid content of less than 2 mass %.

10. A method for improving a subject's learning ability, comprising administering an effective amount of a liver hydrolysate, wherein the liver hydrolysate has (i) a phosphatidylcholine content of less than 0.5 mass %, and (ii) a lipid content of less than 2 mass %.

11. The method of claim 9, wherein the liver hydrolysate has a lipid content of 1 mass % or less.

12. The method of claim 10, wherein the liver hydrolysate has a lipid content of 1 mass % or less.

13. The method of claim 9, wherein the liver hydrolysate has a phosphatidylcholine content of 0.25 mass % or less.

14. The method of claim 10, wherein the liver hydrolysate has a phosphatidylcholine content of 0.25 mass % or less.

* * * * *